United States Patent
Katsman et al.

(10) Patent No.: US 7,418,480 B2
(45) Date of Patent: Aug. 26, 2008

(54) MEDICAL IMAGING DATA STREAMING

(75) Inventors: Igor Katsman, Haifa (IL); Alexander Sokulin, Haifa (IL); Arcady Kempinski, Haifa (IL)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1029 days.

(21) Appl. No.: 10/029,162

(22) Filed: Oct. 25, 2001

(65) Prior Publication Data

US 2003/0083563 A1      May 1, 2003

(51) Int. Cl.
  *G66F 15/16* (2006.01)
  *G06F 19/00* (2006.01)
(52) U.S. Cl. .............. 709/217; 218/219; 218/231; 600/437; 725/115; 382/128; 705/2
(58) Field of Classification Search ......... 709/217–219, 709/231; 600/437; 725/115; 382/128; 705/2
See application file for complete search history.

(56) References Cited

U.S. PATENT DOCUMENTS

| | | | | |
|---|---|---|---|---|
| 5,715,823 A * | 2/1998 | Wood et al. | ............ | 600/437 |
| 5,920,317 A * | 7/1999 | McDonald | ............ | 715/853 |
| 5,949,491 A * | 9/1999 | Callahan et al. | ............ | 348/442 |
| 5,970,457 A * | 10/1999 | Brant et al. | ............ | 704/275 |
| 6,032,120 A * | 2/2000 | Rock et al. | ............ | 705/2 |
| 6,101,407 A * | 8/2000 | Groezinger | ............ | 600/407 |
| 6,224,551 B1 * | 5/2001 | Mullen | ............ | 600/437 |
| 6,275,869 B1 * | 8/2001 | Sieffert et al. | ............ | 719/321 |
| 6,351,547 B1 * | 2/2002 | Johnson et al. | ............ | 382/128 |
| 6,381,029 B1 * | 4/2002 | Tipirneni | ............ | 358/1.14 |
| 6,424,996 B1 * | 7/2002 | Killcommons et al. | ............ | 709/206 |
| 6,519,632 B1 * | 2/2003 | Brackett et al. | ............ | 709/219 |
| 6,656,119 B2 * | 12/2003 | Sasaki et al. | ............ | 600/437 |
| 6,678,764 B2 * | 1/2004 | Parvulescu et al. | ............ | 710/65 |
| 6,807,543 B2 * | 10/2004 | Muthya | ............ | 707/10 |
| 6,839,762 B1 * | 1/2005 | Yu et al. | ............ | 709/230 |
| 6,847,336 B1 * | 1/2005 | Lemelson et al. | ............ | 345/8 |
| 6,928,490 B1 * | 8/2005 | Bucholz et al. | ............ | 709/249 |
| 6,944,631 B2 * | 9/2005 | Peter | ............ | 707/104.1 |
| 7,039,723 B2 * | 5/2006 | Hu et al. | ............ | 709/248 |
| 7,065,588 B2 * | 6/2006 | Konda et al. | ............ | 709/246 |
| 7,072,931 B2 * | 7/2006 | Goldhaber et al. | ............ | 709/201 |
| 7,127,499 B1 * | 10/2006 | Accardi et al. | ............ | 709/219 |
| 7,139,417 B2 * | 11/2006 | Nicolas et al. | ............ | 382/131 |
| 7,143,149 B2 * | 11/2006 | Oberg et al. | ............ | 709/220 |

(Continued)

*Primary Examiner*—Nathan Flynn
*Assistant Examiner*—Alina N. Boutah
(74) *Attorney, Agent, or Firm*—McAndrews, Held & Malloy, Ltd.; Peter J. Vogel; Michael A. Dellapenna

(57) ABSTRACT

A system and method for streaming unprocessed medical image data from a medical imaging system to a remote terminal is provided. A medical imaging system acquires medical image data, generates unprocessed medical image data, and then transmits the unprocessed medical image data to a remote terminal. The remote terminal receives the unprocessed medical image data, processes the data to render a medical image and displays the medical image to an operator at the remote terminal. Additionally, the operator may control imaging parameters at the remoter terminal for use in rendering the medical image. Additionally, the operator may control imaging parameters on the medical imaging system. Also, the operator at the remoter terminal and the operator at the medical imaging system may communicate with each other during the examination through the medical imaging system.

17 Claims, 3 Drawing Sheets

U.S. PATENT DOCUMENTS

| | | | |
|---|---|---|---|
| 7,149,779 B2 * | 12/2006 | Bocionek | 709/206 |
| 2002/0023172 A1 * | 2/2002 | Gendron et al. | 709/238 |
| 2002/0029264 A1 * | 3/2002 | Ogino et al. | 709/223 |
| 2002/0087664 A1 * | 7/2002 | Birkhoelzer et al. | 709/219 |
| 2002/0156864 A1 * | 10/2002 | Kniest | 709/217 |
| 2003/0005464 A1 * | 1/2003 | Gropper et al. | 725/115 |
| 2003/0097054 A1 * | 5/2003 | Sasaki et al. | 600/407 |
| 2004/0260790 A1 * | 12/2004 | Balloni et al. | 709/219 |

* cited by examiner

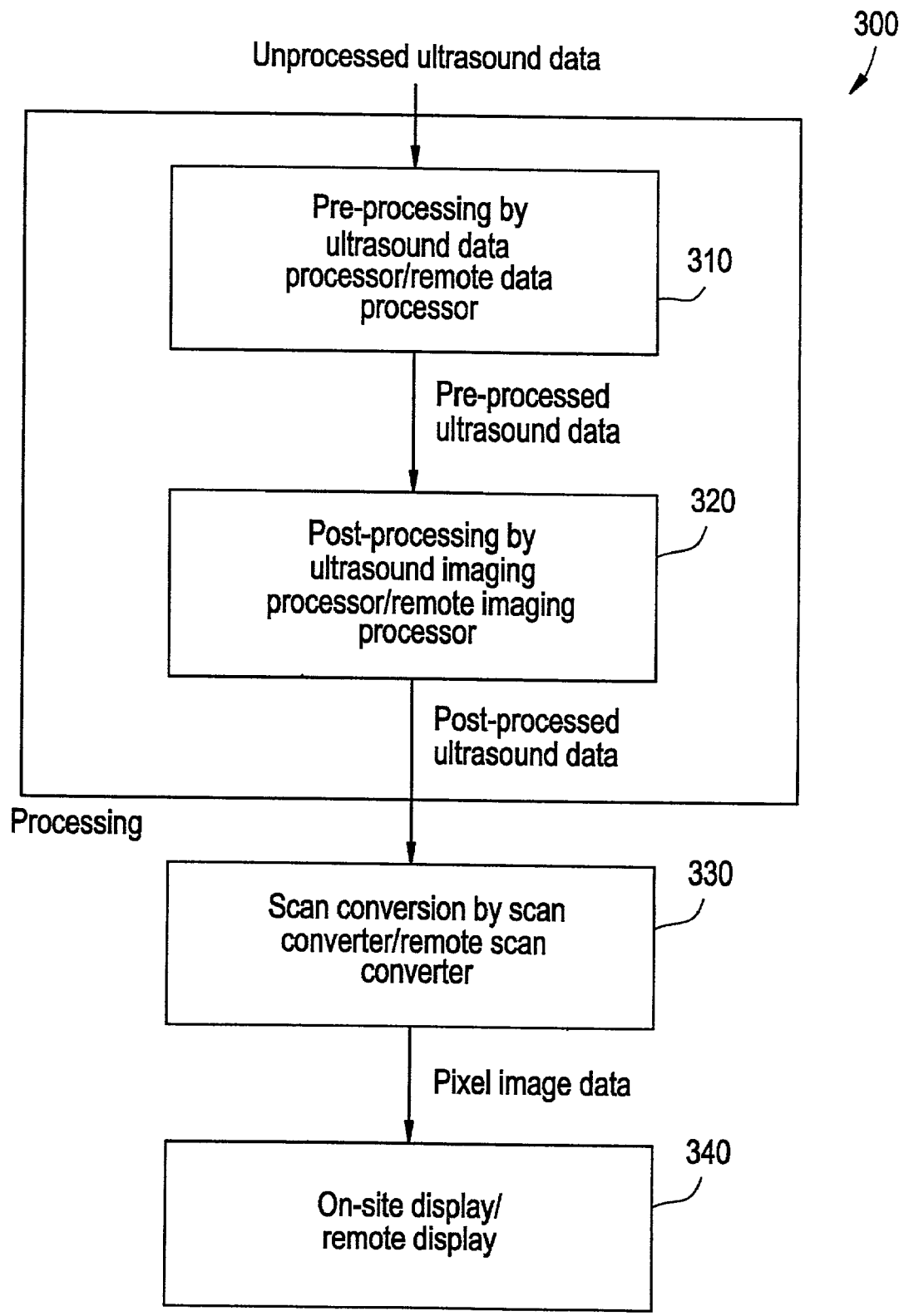

MEDICAL IMAGING DATA STREAMING

BACKGROUND OF THE INVENTION

The present invention generally relates to a system and method for transmitting medical imaging data. More particularly, the present invention relates to transmitting remotely controllable unprocessed medical imaging data over a network such as the Internet, an Intranet, or a wireless network to a remote site for viewing by an expert.

Medical imaging systems are typically used for a wide variety of applications in the field of medicine. For example, medical imaging systems such as ultrasound, CT scan, MRI, or X-ray systems, may be used for diagnosis or monitoring purposes. One type of medical imaging system commonly used in medicine is an ultrasound imaging system. Typical ultrasound imaging systems operate by transmitting ultrasonic sound waves into a patient's body using a transducer. The transducer is typically a device placed on the patient's body over the area to be imaged that is capable of sending and receiving ultrasonic sound waves. The ultrasonic sound waves sent by the transducer are reflected by the patient's internal bodily structures. The reflected ultrasonic sound waves transmitted into the patient's body may then be received by the transducer and transmitted to a data acquisition processor in the ultrasound imaging system.

The data acquisition processor typically converts the ultrasonic sound waves into digital, unprocessed ultrasound data. The unprocessed ultrasound data may then be transmitted to an ultrasound data processor. The ultrasound data processor may then perform pre-processing functions on the unprocessed ultrasound data resulting in pre-processed ultrasound data. The pre-processed ultrasound data may then be transferred to an ultrasound imaging processor in the ultrasound imaging system. The ultrasound imaging processor may then perform post-processing functions such as B-compression, dynamic range adjustments, or intensity threshold, for example, on the pre-processed ultrasound data resulting in post-processed ultrasound data. The post-processed data may then be transmitted to a scan converter. The scan converter of the post-processed ultrasound data may convert the post-processed ultrasound data into pixel image data in X-Y coordinates. The pixel image data may then be transmitted to a display console. The display console typically displays the final pixel image data so that a visual representation of the patient's internal bodily structures may be viewed or heard as an ultrasound image in real time by a doctor or technician for example.

Typical ultrasound imaging systems may also include a control console. The control console of the ultrasound imaging system typically includes a number of control devices. The control devices of the control console may be used by the technician or doctor to manipulate the parameters of the pre-processed or post-processed ultrasound data. The manipulation of the parameters of the pre-processed or post-processed ultrasound data allows the technician to adjust or manipulate the displayed ultrasound images. Ultrasound imaging systems that allow the technician or an examining doctor to adjust or manipulate the displayed ultrasound images may provide for greater flexibility and control over an ultrasound examination. Typically, the examining doctor knows what ultrasound images need to be viewed and the how the ultrasound images need to be viewed in order to make an accurate diagnosis. Thus, by allowing the examining doctor to manipulate the displayed ultrasound images, the doctor can get the information and images needed to make an accurate diagnosis. However, not all ultrasound examinations may actually be performed with a doctor in the examination room.

In today's highly specialized medical society, expert doctors or specialists with skills in specific fields such as ultrasound examination and diagnosis for example, may not be available at every medical facility with ultrasound imaging systems. Specialists in ultrasound imaging may be particularly hard to find at medical facilities in remote or rural areas. Thus, traditionally, in rural areas where specialists were not available to perform an ultrasound examination, either the specialist may have been transported to the rural location, or the patient may have been transported to the specialist's location. However, transporting the specialist to the rural area may be undesirable because transportation of the specialist may be time consuming or expensive. Additionally, transporting the patient may also be undesirable because transportation of the patient may also be time consuming or possibly dangerous. Therefore, in response to the fact that not all medical facilities with ultrasound imaging systems may have specialists on-site, remotely viewable ultrasound imaging systems have been developed. Remotely viewable ultrasound imaging systems typically allow a remotely located specialist to view ultrasound images taken from an on-site ultrasound imaging system. That is, a technician may actually perform the ultrasound procedure on-site, while an ultrasound specialist may view the ultrasound images at a remote location.

Typical remotely viewable ultrasound imaging systems may operate by transmitting the scan converted pixel image data over an Internet connection from the on-site facility to the remote location. The pixel image data may typically be compressed on-site using a video data compression format such as MPEG for example, and then transmitted over the Internet to the remote location. At the remote location, a remote terminal may be used to decode the compressed data and display the ultrasound images to the remote specialist. The remote specialist may then be able to diagnose or view the ultrasound images being taken and manipulated by the technician. While typical remotely viewable ultrasound imaging systems may allow a remotely located specialist to view ultrasound data, typical systems may suffer from some significant drawbacks.

One drawback that may exist in typical remotely viewable ultrasound imaging systems is a choppy video feed or transmission lag. Typical scan conversion functions performed on the post-processed ultrasound data by the ultrasound data processor as discussed above, may result in a significant increase in the size of the ultrasound data. For example, one video frame of unprocessed ultrasound data may represent approximately 50 kilobits of data, while one frame of scan converted post-processed ultrasound data may represent approximately 1 megabyte of data. Typical ultrasound imaging systems may display video at 30 or more frames per second for real time video. Thus, transmitting the relatively large pixel image data over the limited bandwidth of an Internet connection may result in a transmission lag, or transmission of data at a slower rate than required for real time video at 30 framer per second. Delivering video data at a slower rate than required for real time video at 30 frames per second may result in reduced frame rates, which may result in a choppy video stream. A choppy video stream may be undesirable in ultrasound imaging systems because real time imaging is highly desirable for allowing the specialist to make accurate diagnoses or readings of the ultrasound image.

An additional drawback that may exist in typical remotely viewable ultrasound imaging systems is loss of image quality. Because of the limited bandwidth available over the Internet and the relatively large size of the pixel image data as discussed above, the pixel image data may typically be significantly compressed by hardware or software prior to transmission to the remote location. Typical lossy video compression algorithms such as MPEG may result in lost data during the transfer from the on-site location to the remote location. Thus, when the remote viewer decompresses the compressed data, degradation in image quality may occur as a result of the lost data. Degradation in image quality may be undesirable in ultrasound imaging systems because high quality images are highly desirable for allowing the specialist to make accurate diagnoses or readings of the ultrasound image. In order to fit the given bandwidth, the compression ratio typically must be high which results in a higher data loss in many cases.

Another drawback that may exist in typical remotely viewable ultrasound imaging systems is the lack of control over the ultrasound examination by the remotely located specialist. Because the remote terminal typically receives the pixel image data after it has been scan converted, the remote specialist may not be able to perform many of the pre-processing or post-processing functions or operations on the ultrasound data available to the technician performing the ultrasound imaging. The technician performing the ultrasound imaging may typically be able to manipulate or adjust the parameters of the pre-processed and post-processed ultrasound data using the on-site console controls of the ultrasound imaging system as discussed above. However, since the remote specialist receives the pixel image data at such a late stage in the data cycle, the remote specialist may typically be unable to adjust the pre-processing or post-processing functions such as B-compression, dynamic range adjustments, or intensity threshold for example, from the remote terminal. Instead, the remote specialist may only be able to adjust the viewing parameters of the ultrasound image such as contrast, smoothness, brightness, or resizing for example, at the remote terminal. Thus, the remote specialist may be restricted to viewing the ultrasound images as dictated by the technician performing the ultrasound examination.

Also, because an unskilled technician may not know what may be important to display to the remote specialist, the unskilled technician may transmit less than optimal ultrasound images to the remote expert which may result in difficult diagnoses or inaccurate diagnoses by the remote specialist. Thus, the lack of control of the imaging operation on the part of the remote specialist is a considerable drawback. Additionally, it would be highly desirable to provide remote specialist with the ability to control at least part of the imaging operation because typically only the remote specialist typically knows what ultrasound images are desired to be viewed and how to view the images in order to make an accurate diagnosis.

Thus, a need exists for a medical imaging system the provides real-time, high resolution images to a remote expert for evaluation. Additionally, due to the drawbacks discussed above that may occur in typical remotely viewable ultrasound imaging systems, a need exists for a remotely viewable medical imaging system capable of transmitting smooth, high quality, real time ultrasound data to a remote terminal. Also, a need exists for such a medical imaging system that allows a remote expert to exert at least some control over the imaging operation. More specifically, a need further exists for a remotely viewable medical imaging system that allows a remotely located operator to have the same control over the functionality of the medical imaging system as the technician performing the ultrasound imaging.

BRIEF SUMMARY OF THE INVENTION

The preferred embodiment of the present invention provides a system and method for remotely viewing and controlling an ultrasound imaging device. The present invention preferably includes an ultrasound imaging system and a remote terminal. In operation, a technician performs an ultrasound examination on a patient by using a transducer connected to the ultrasound imaging system. The ultrasonic signals received by the transducer are transmitted to a data acquisition processor in the ultrasound imaging system. The data acquisition processor converts the ultrasonic sound waves into digital, unprocessed ultrasound data. An ultrasound data processor then performs pre-processing functions on the unprocessed to form pre-processed ultrasound data. The pre-processed ultrasound data is then preferably transmitted to an ultrasound imaging processor. The ultrasound imaging processor may then perform post-processing functions on the pre-processed ultrasound data resulting in post-processed ultrasound data. The post-processed ultrasound data is the preferably scan converted into pixel image data and transmitted to a display where the pixel image data may be viewed as an ultrasound image. However, prior to pre-processing by the ultrasound data processor, the unprocessed ultrasound data, as well as system parameter data, is compressed and transmitted over a network connection, such as an Internet connection, to the remote terminal.

At the remote terminal, the unprocessed ultrasound data is received by a remote data processor and decompressed. The remote data processor may then perform pre-processing functions on the unprocessed ultrasound data resulting in pre-processed ultrasound data. The pre-processed ultrasound data is then preferably transmitted to a remote imaging processor. The remote imaging processor may then perform post-processing functions on the pre-processed ultrasound data resulting in post-processed ultrasound data. A doctor or ultrasound-imaging specialist at the remote terminal may use remote console controls to manipulate the pre-processing or post-processing functions performed on the processed ultrasound data. Once the ultrasound data is pre-processed and post-processed to the desired parameters by the doctor, the post-processed ultrasound data and system parameter data is then preferably scan converted resulting in image pixel data. The image pixel data is then preferably transmitted to a remote display of the remote terminal for viewing by the doctor.

Additionally, the remote specialist may use the remote console controls to transmit commands back to the ultrasound imaging system. The commands may be used to manipulate the pre-processing or post-processing functions of the ultrasound data processor. Thus, the remotely located doctor may exert considerable control over the pre-processing and post-processing functions of the ultrasound data processor.

BRIEF DESCRIPTION OF THE DRAWINGS

FIG. 3 illustrates a flowchart of the data conversion flow of the remotely controllable ultrasound imaging system according to a preferred embodiment of the present invention.

DETAILED DESCRIPTION OF THE INVENTION

Figure 1:
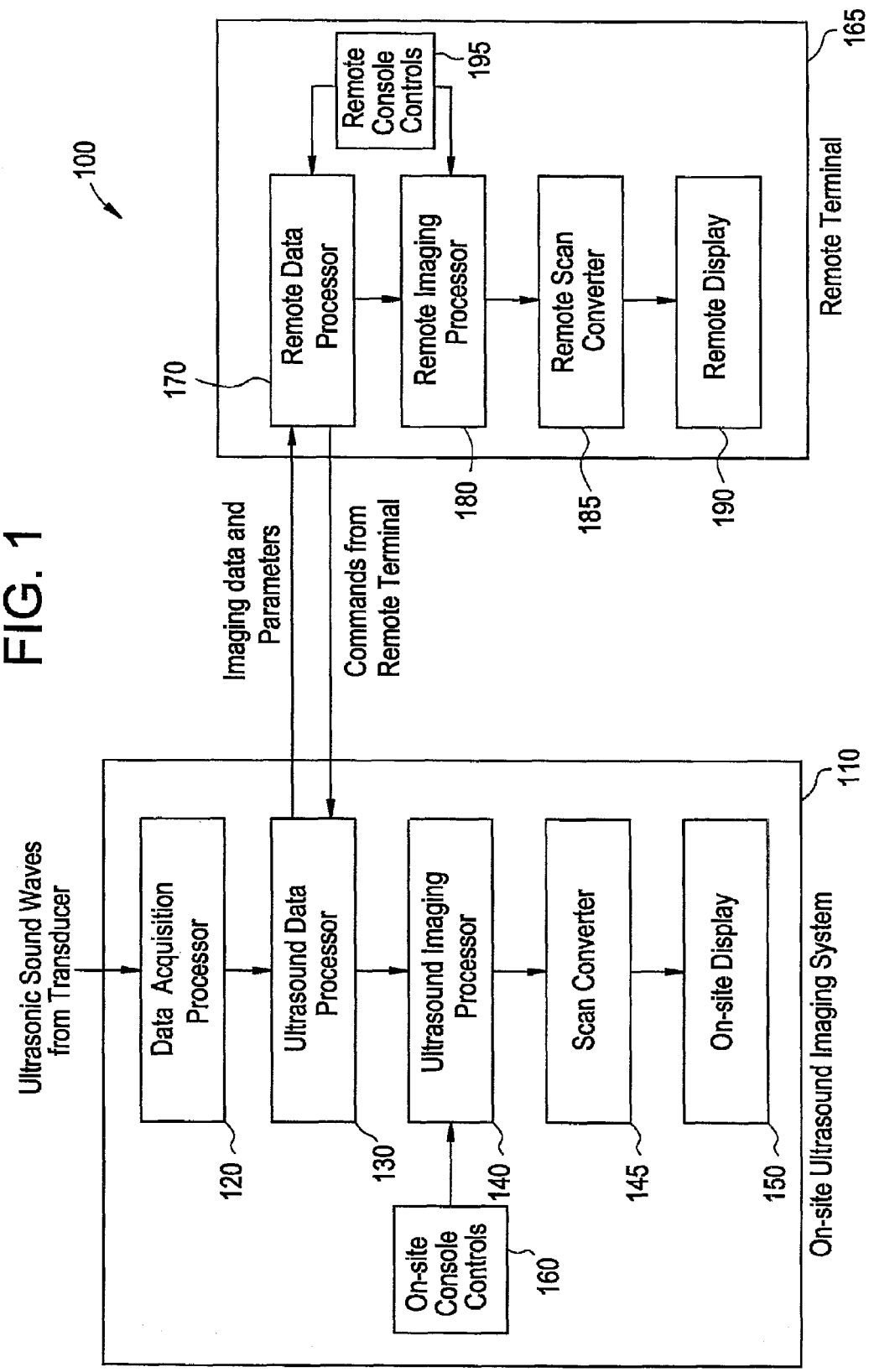
FIG. 1 illustrates a remotely controllable ultrasound imaging system according to a preferred embodiment of the present invention.

FIG. 1 illustrates a remotely controllable ultrasound imaging system 100 according to a preferred embodiment of the present invention. The imaging system 100 includes an ultrasound imaging system 110 and a remote terminal 165. The ultrasound imaging system includes a data acquisition processor 120, an ultrasound data processor 130, an ultrasound imaging processor 140, a scan converter 145, an on-site display 150, and on-site console controls 160. The remote terminal 165 includes a remote data processor 170, a remote imaging processor 180, a remote scan converter 185, a remote display 190, and remote console controls 195.

The ultrasound imaging system 110 of the remotely controllable ultrasound imaging system 100 is preferably attached to a transducer (not shown). The transducer is connected to an input port of the ultrasound imaging system 110. The data acquisition processor 120, the ultrasound data processor 130, the ultrasound imaging processor 140, and the scan converter 145, are preferably located inside a housing (not shown) of the ultrasound imaging system 110. The on-site display 150 is preferably attached to the ultrasound imaging system 110 in a position viewable by an operator. Similarly, the on-site console controls 160 are also preferably attached to the ultrasound imaging system 110 in a position reachable by the operator.

The remote terminal 165 of the remotely controllable ultrasound imaging system 100 is preferably attached to the ultrasound imaging system 110 by a network connection such as an Internet, Intranet, or wireless network connection for example. The remote data processor 170, the remote imaging processor 180, and the remote scan converter 185 are preferably located inside a housing (not shown) of the remote terminal 165. The remote display 190 is preferably attached to the remote terminal 165 in a position viewable by an operator. The remote console controls 195 are also preferably attached to the remote terminal 165 in a position reachable by the operator.

In operation, a technician and a patient are preferably located at the site of the ultrasound imaging system 110. A doctor or ultrasound-imaging specialist is preferably located at a remote site with the remote terminal 165. Once a network connection, such as an Internet, Intranet, or wireless connection for example, is established between the ultrasound imaging system 110 and the remote terminal 165, the ultrasound imaging may begin. To perform the ultrasound imaging, the technician preferably positions a transducer on the patient to image the desired area of the patient's body. As discussed in the background section above, the transducer transmits ultrasonic sound waves into the patient's body. The ultrasonic sound waves sent by the transducer into the patient's body are reflected by the patient's internal bodily structures. The reflected ultrasonic sound waves transmitted into the patient's body may then be received by the transducer and are then preferably transmitted to the data acquisition processor 120 of the ultrasound imaging system 110 as illustrated in FIG. 1.

The data acquisition processor 120 preferably converts the analog ultrasonic sound waves into digital, unprocessed ultrasound data. The unprocessed ultrasound data is then preferably transmitted to the ultrasound data processor 130. The ultrasound data processor 130 then preferably performs pre-processing functions such as calculating the mathematical functions to transform the ultrasound data from one for to another for example, on the unprocessed ultrasound data. However, prior to pre-processing, the unprocessed ultrasound data is preferably transmitted from the ultrasound imaging system 110 to the remote terminal 165 over the network connection. Prior to transmission over the network connection, the unprocessed ultrasound data is preferably compressed by the ultrasound imaging system 110 using a data compression algorithm such as MPEG, for example. Since the amount of unprocessed ultrasound data required for real-time imaging is typically significantly smaller than the amount of pixel image data transmitted in typical prior art systems, the unprocessed ultrasound data may be compressed using a lossless compression format or with a smaller compression ratio, thus resulting in a smaller data loss. The data may even be transmitted uncompressed given a network connection of sufficient bandwidth, if desired. Upon transmission over the network, the compressed unprocessed ultrasound data is preferably received by the remote data processor 170 of the remote terminal 165.

In addition to transmitting the unprocessed ultrasound data from the ultrasound imaging system 110 to the remote terminal 165, a second stream of system parameter data is also preferably compressed and synchronously transmitted with the unprocessed ultrasound data. The system parameter data may be generated by the ultrasound data processor, Input from on-site controls, or both for example. The system parameter data may include information such as patient name, patient ID, system state, or other information for example. The system parameter data is also preferably received by the remote data processor 170 of the remote terminal 165.

Once the remote data processor 170 of the remote terminal 165 receives the unprocessed ultrasound data and the system parameter data, the remote data processor 170 preferably decompresses the unprocessed ultrasound data and the system parameter data, if any. The remote data processor 170 may then perform pre-processing functions on the unprocessed data as discussed above, resulting in pre-processed ultrasound data. The pre-processed ultrasound data is then preferably transmitted to the remote imaging processor 180. The remote imaging processor 180 then preferably performs post-processing functions such as B-compression, dynamic range adjustments, or intensity threshold, for example, on the pre-processed ultrasound data resulting in post-processed ultrasound data.

The doctor or ultrasound-imaging specialist at the remote terminal 165 may use the remote console controls 195 to manipulate the pre-processing or post-processing functions performed on the unprocessed ultrasound data. By receiving the ultrasound data in an unprocessed format, the doctor or ultrasound-imaging specialist may perform all of the pre-processing or post-processing functions at the remote terminal 165 that the ultrasound technician may perform at the ultrasound imaging system 110. Once the unprocessed ultrasound data is pre-processed and post-processed to the desired parameters by the doctor, the post-processed ultrasound data and system parameter data are preferably transmitted to the remote scan converter 185. The remote scan converter 185 then preferably performs a scan conversion on the post-processed ultrasound data. The scan conversion of the post-processed ultrasound data preferably converts the post-processed ultrasound data into pixel image data in X-Y coordinates. The pixel image data and the system parameter data are then preferably transferred to the remote display 190 of the remote terminal 165. The remote display 190 preferably displays the pixel image data and the system parameter data as images so that the doctor or ultrasound-imaging specialist may view a visual representation of the patient's internal bodily structures as well as patient information in real time.

As the unprocessed ultrasound data transmitted to the remote terminal 165 is being processed at the remote terminal 165 by the methods discussed above, the unprocessed ultrasound data is also preferably being simultaneously processed at the ultrasound imaging system 110. That is, upon transmission of the unprocessed ultrasound data to the remote terminal 165, the unprocessed ultrasound data also preferably continues to be processed at the ultrasound imaging system 110. The unprocessed ultrasound data is processed at the ultrasound imaging system 110 in substantially the same fashion as the unprocessed ultrasound data is processed at the remote terminal 165 as further discussed below.

As previously discussed with regard to the remote terminal 165, the data acquisition processor 120 of the ultrasound imaging system 110 converts the ultrasonic sound waves into digital, unprocessed ultrasound data. The unprocessed ultrasound data is then preferably transmitted to the ultrasound data processor 130. As discussed above, prior to pre-processing, the unprocessed ultrasound data is preferably compressed and transmitted to the remote terminal 165. After one stream of the unprocessed ultrasound data is transmitted to the remote terminal 165, a second stream of unprocessed ultrasound data is preferably pre-processed by the ultrasound data processor 130 resulting in pre-processed ultrasound data. The pre-processed ultrasound data is then preferably transmitted to the ultrasound imaging processor 140. The ultrasound imaging processor 140 then preferably performs post-processing functions such as B-compression, dynamic range adjustments, or intensity threshold, for example, on the pre-processed ultrasound data resulting in post-processed ultrasound data.

The technician at the ultrasound imaging system 110 may use the on-site console controls 160 to manipulate the pre-processing or post-processing functions performed on the unprocessed ultrasound data. Once the unprocessed ultrasound data is pre-processed and post-processed to the desired parameters by the technician, the post-processed ultrasound data and system parameter data are preferably transmitted to the scan converter 145. The scan converter 145 then preferably performs a scan conversion on the post-processed ultrasound data. As discussed above, the scan conversion of the post-processed ultrasound data preferably converts the post-processed ultrasound data into pixel image data in X-Y coordinates. The pixel image data and the system parameter data are then preferably transferred to the on-site display 150 of the ultrasound imaging system 110. The on-site display 150 preferably displays the pixel image data and the system parameter data as images so that the technician and the patient may view a visual representation of the patient's internal bodily structures as well as patient information in real time.

In a preferred embodiment of the present invention, the network connection between the ultrasound imaging system 110 and the remote terminal 165 is bi-directional. That is, the ultrasound data processor 130 preferably transmits unprocessed ultrasound data to the remote data processor 170 while the remote data processor 170 may transmit command data back to the ultrasound data processor 130 as illustrated in FIG. 1. The command data transmitted to the ultrasound data processor 130 by the remote data processor 170 may be used to adjust the pre-processing or post-processing functions of the ultrasound imaging system 110. Thus, the remotely located specialist may control the parameters of the unprocessed ultrasound data being transmitted to the remote data processor 170 even prior to transmission. Allowing the remotely located specialist to control the parameters of the unprocessed ultrasound data even prior to transmission gives the specialist substantially the same level of control and flexibility over the ultrasound imaging as the technician performing the ultrasound imaging.

Additionally, the command data transmitted to the ultrasound data processor 130 by the remote data processor 170 may also include the post-processing parameters of the remote imaging processor 180. Thus, the changes in the post-processing parameters made by the specialist at the remote terminal 165 may be transmitted back to the ultrasound imaging system 110 and duplicated by the ultrasound imaging processor 140. Therefore, the technician may view the ultrasound images on the on-site display 150 as manipulated by the specialist at the remote terminal 165. Allowing the technician to view the ultrasound images as dictated by the specialist may aid the technician in determining what the specialist determines is important and allow the technician to alter the ultrasound examination appropriately.

In an alternative embodiment of the present invention, two-way audio data may also be transmitted over the network connection between the ultrasound imaging system 110 and the remote terminal 165. In the alternative embodiment, the ultrasound imaging system 110 additionally includes a microphone, a speaker, and a speech recognition and processing system. Similarly, the remote terminal 165 also additionally includes a microphone, a speaker, and a speech recognition and processing system.

In operation, the specialist at the remote terminal 165 may speak into the microphone of the remote terminal 165. The microphone then transmits the audio signal to the speech recognition and processing system of the remote terminal 165. The speech recognition and processing system converts the specialist's speech into digital speech data. The digital speech data may then be transmitted to the remote data processor 170. The remote data processor 170 may then compress the digital speech data using the MPEG format for example. The compressed digital speech data may then be transmitted from the remote terminal 165 to the ultrasound data processor 110 over the network connection. The ultrasound data processor 130 may then receive and decompress the digital speech data from the remote terminal 165. The decompressed digital speech data may then be transmitted to the speech recognition and processing system of the ultrasound imaging system 110. The speech recognition and processing system of the ultrasound imaging system 110 may then process the digital speech data and transmit the digital speech data to the speaker. The speaker may then display the digital speech data as an audio signal able to be heard by the technician at the ultrasound imaging system.

Alternatively, the specialist's voice signals may be directly digitized at the remote data processor 170 to form a digital voice signal. The digital voice signal may then be transmitted from the remote terminal 165 to the ultrasound data processor 110 over the network connection. The ultrasound data processor 130 may then receive and decompress the digital voice signal and then transmit the digital voice signal to the speaker.

The technician may also transmit audio signals, or speech, to the specialist in substantially the same manner as described above. Allowing the technician and the specialist to speak to each other during the ultrasound imaging examination may allow the specialist to give instructions to the technician during the examination. Thus, allowing communication between the technician and the specialist during the examination may allow for more accurate and efficient ultrasound examinations.

In a third alternative embodiment of the present invention, two-way ultrasound image annotation data may also be transmitted over the network connection between the ultrasound imaging system 110 and the remote terminal 165. In the third alternative embodiment, the on-site console controls 160 and the remote console controls 195 may include a stylus or other control device that may be used to draw on or annotate the ultrasound images on the on-site display 150 and the remote display 190.

In operation, the specialist may use the remote console controls 195 to make annotations on the ultrasound image being displayed on the remote display 190. The annotations made by the specialist on the remote display 190 may then be transmitted over the network to the ultrasound imaging system 110 and displayed on the on-site display 150 for the technician to view in substantially the same manner as discussed above with regard to the preferred embodiment. Thus, for example, the specialist may highlight areas of interest on the ultrasound image for the technician to focus the examination. The technician may also annotate the ultrasound image on the on-site display 150 and transmit the annotations over the network to the remote terminal 190 for the specialist to view on the remote display 190. Allowing the specialist and the technician to annotate the ultrasound images and view each other's annotations, may increase the level of interaction between the specialist and the technician which may improve the efficiency and quality of the ultrasound examination.

While the preferred embodiment of the present invention has been described with reference to an ultrasound imaging system that transmits ultrasound imaging data, the ultrasound data collected by the transducer and transmitted and displayed at the remote terminal 165 may also include Doppler audio data.

Additionally, while the preferred embodiment of the present invention has been described with reference to an ultrasound imaging system, the invention may be employed in any type of medical imaging system where it is desirable for a remotely located expert to view a medical image or control the functionality of the medical imaging system.

Figure 2:
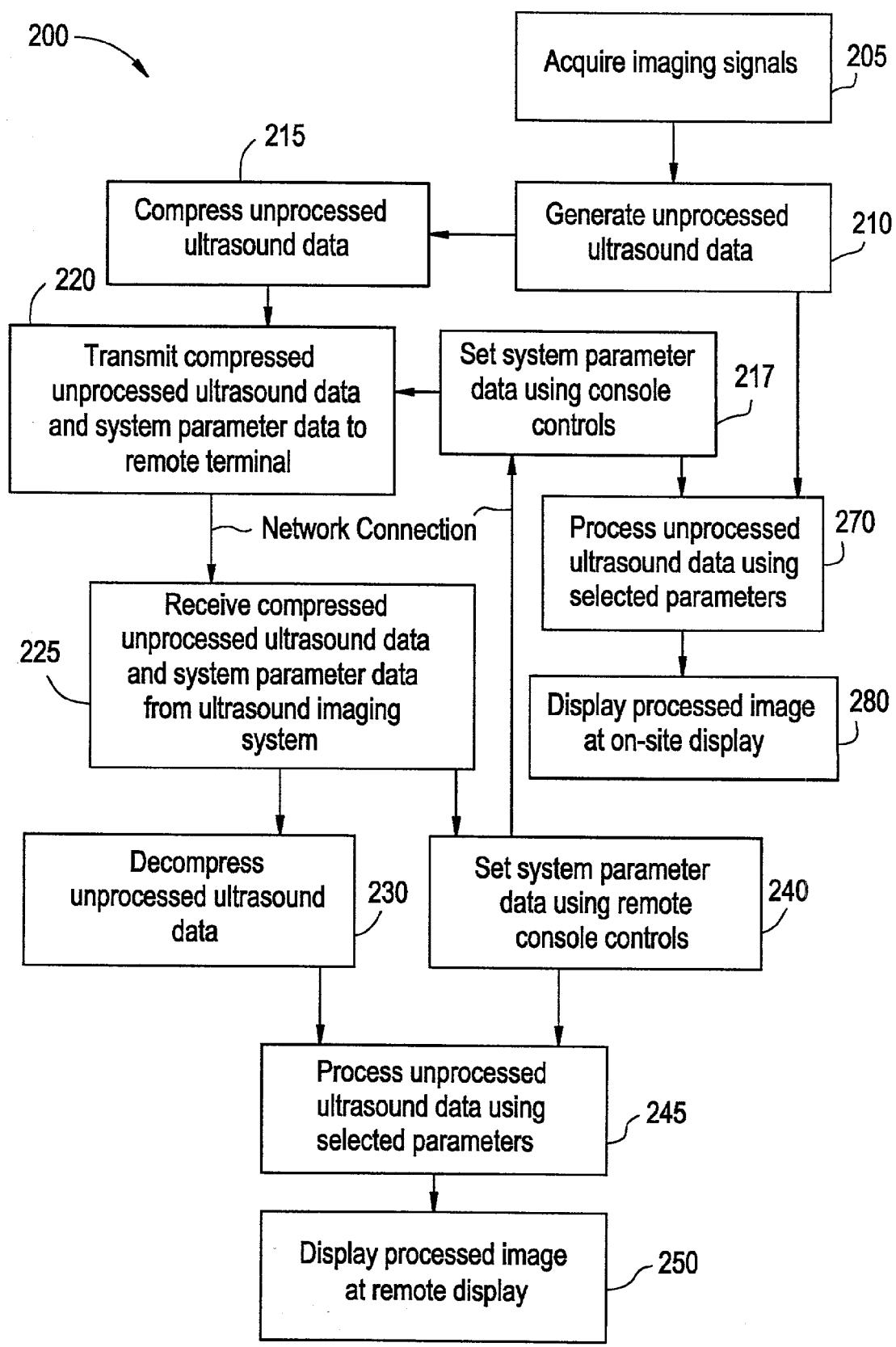
FIG. 2 illustrates a flowchart of the remotely controllable ultrasound imaging system according to a preferred embodiment of the present invention.

FIG. 2 illustrates a flowchart 200 of the remotely controllable ultrasound imaging system according to a preferred embodiment of the present invention. First, at step 205, imaging signals are acquired by a medical imaging system. For example, ultrasonic signals from an ultrasonic transducer may be acquired by an ultrasonic imaging system. Next, at step 210, the imaging signals acquired by the medical imaging system are operated upon by the medical imaging system to generate unprocessed imaging data. For example, the ultrasonic signals may be acquired by the ultrasonic imaging system may be digitized and/or otherwise manipulated to generate unprocessed ultrasonic imaging data. Then, at step 215, the unprocessed imaging data is compressed. The imaging data may be compressed using any of a variety of lossy or lossless compression techniques known in the art.

Next, at step 217, system parameter data from the imaging system is set using the console controls. At step 220, the unprocessed imaging data and the parameter data are transmitted from the medical imaging system to a remote terminal. The transmission may occur over any type of transmission network, but preferably occurs via a high-speed network such as wireless, DSL (Digital Subscriber Line), or other broadband network.

Then, at step 225, the compressed unprocessed ultrasound data and system parameter data are received by the remote terminal. At step 230, the unprocessed imaging data is decompressed at the remote terminal. Additionally, if parameter data was compressed with the imaging data, the parameter data is also decompressed. At step 240, an operative set of imaging parameters at the remote terminal is acquired. The set of imaging parameters may have been entered by an operator, such as a medical specialist, at the remote terminal controls. The set of imaging parameters acquired at step 240 may also be transmitted back from the remote imaging system to the medical imaging system previously described at step 217. For example, the operator may transmit commands to either the imaging system or an operator of the imaging system. For example, as discussed above, the operator of the remote terminal may instruct the operator of the imaging system to concentrate the image on a certain area of a patient's body. Alternatively, the operator of the remote terminal may communicate with the operator of the imaging system using image annotations or voice commands, as described above.

Then, at step 245, the remote terminal applies the set of imaging parameters to process the unprocessed imaging data to develop an processed image. Concurrent with step 245, at step 270, the medical imaging system applies the set of imaging parameters to process the unprocessed imaging data to develop an processed image. Next, at step 250, the processed image is displayed at the remote terminal for review by an operator. Also concurrent with step 250, at step 280, the processed image is displayed at the medical imaging system for review by an operator. Next, at step 255, after viewing the image, the operator may alter the imaging parameters at the remote terminal as shown. For example, as the remote terminal continues to receive streaming data from the imaging system, the operator may control parameters to increase or decrease the dynamic range of the processed image displayed at the remote terminal.

FIG. 3 illustrates a flowchart 300 of the data conversion flow of the remotely controllable ultrasound imaging system according to a preferred embodiment of the present invention. The data conversion flow of the remotely controllable ultrasound imaging system begins with unprocessed ultrasound data. As described above with regard to the detailed description, the unprocessed ultrasound data is preferably acquired by a transducer attached to the ultrasound imaging system. At step 310, the unprocessed ultrasound data is preferably pre-processed concurrently at the ultrasound imaging system and the remote terminal by the ultrasound data processor and the remote data processor respectively as described above in FIG. 1. Pre-processing functions may include calculating the mathematical functions to transform the unprocessed ultrasound data from one for to another for example. The pre-processing functions performed by the ultrasound data processor and the remote data processor convert the unprocessed ultrasound data into pre-processed ultrasound data.

Then, at step 320, the pre-processed ultrasound data is preferably post-processed concurrently at the ultrasound imaging system and the remote terminal by the ultrasound imaging processor and the remote imaging processor respectively as described above in FIG. 1. Post-processing functions may include B-compression, dynamic range adjustments, or intensity threshold, for example. The post-processing functions performed by the ultrasound imaging processor and the remote imaging processor convert the pre-processed ultrasound data into post-processed ultrasound data.

Upon being pre-processed and post-processed, at step 330, the post-processed ultrasound data is preferably scan converted concurrently at the ultrasound imaging system and the remote terminal by the scan converter and the remote scan converter respectively as described above in FIG. 1. The scan conversion performed by the scan converter and the remote scan converter convert the post-processed ultrasound data into pixel image data. As discussed above, the pixel image data is preferably X-Y position coordinate data. Finally, at step 340, the pixel image data is preferably displayed as an image by the on-site display and the remote display respectively as described above in FIG. 1.

Thus, the remotely controllable ultrasound imaging system 100 presented in the present invention provides for the real-time transmission of high resolution medical images to a remote expert for evaluation. Additionally, a preferred embodiment of the present invention provides for a remotely viewable medical imaging system capable of transmitting smooth, high quality, real time ultrasound data to a remote terminal. Furthermore, the medical imaging system presented in the present invention allows a remote expert to have the same control over the functionality of the medical imaging system as the technician performing the ultrasound imaging. Allowing the remote expert to have same level of control and flexibility over the ultrasound imaging as the technician performing the ultrasound imaging may improve the quality, efficiency, and accuracy of the ultrasound examination which may result in improved patient care and reduced medical costs.

While the present invention has been described above with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A system for remotely displaying a medical image, said system including:
    a medical imaging system transmitting unprocessed medical imaging data to a remote terminal; and
    a remote terminal for receiving said unprocessed medical imaging data, processing said unprocessed medical imaging data according to preferences and control of an operator at said remote terminal, scan converting said processed image data into pixel image data to form a medical image and displaying said medical image at said remote terminal,
    wherein said remote terminal sends commands to said medical imaging system to affect operation of said medical imaging system to acquire and process medical imaging data.

2. The system of claim 1 wherein said remote terminal performs post-processing on said unprocessed medical image data.

3. The system of claim 1 wherein said medical imaging system acquired said unprocessed medical imaging data.

4. The system of claim 1 wherein said medical imaging system also transmits audio data to said remote terminal.

5. The system of claim 1 wherein said medical imaging system also transmits system parameter data to said remote terminal.

6. The system of claim 1 wherein said commands sent from said remote terminal to said medical imaging system control at least one of pre-processing functions and post-processing functions of said medical imaging system.

7. The system of claim 1 wherein said operator at said remote terminal has the same control of said medical imaging system as a user at said medical imaging system.

8. A system for remotely post-processing medical imaging data, said system including:
    a remote terminal receiving unprocessed medical imaging data, said remote terminal including a remote imaging processor receiving said unprocessed medical imaging data and post-processing said medical imaging data, said remote terminal processing said unprocessed medical imaging data according to imaging parameters, said imaging parameters controlled by an operator at said remote terminal,
    wherein said remote terminal scan converts said processed medical imaging data into pixel image data to form a medical image and displays said medical image at said remote terminal.

9. The system of claim 8 wherein said unprocessed medical imaging data is sent by a medical imaging system to said remote terminal.

10. A remote terminal for use in a medical imaging system for remotely displaying a medical image, said remote terminal including:
    a remote data processor receiving unprocessed medical imaging data and pre-processing said unprocessed medical imaging data according to preferences and control of an operator at said remote terminal;
    a remote imaging processor post-processing said pre-processed medical imaging data and scan converting said post-processed medical imaging data into pixel image data to form a medical image according to preferences and control of said operator at said remote terminal;
    remote console controls controlling imaging parameters at said remote imaging processor and relaying commands relating to acquisition and processing of medical imaging data through said remote data processor to an imaging system; and
    a display for displaying said medical image.

11. A method for remotely displaying a medical image, said method including the steps of:
    transmitting unprocessed medical imaging data from a medical imaging system to a remote terminal;
    processing said unprocessed medical imaging data at said remote terminal according to preferences and control of an operator at said remote terminal;
    scan converting said processed medical imaging data into pixel image data to form a medical image according to preferences and control of said operator at said remote terminal;
    sending commands related to image data processing from said remote terminal to said medical imaging system; and
    displaying said medical image.

12. The method of claim 11 further including the step of post-processing said unprocessed medical image data at said remote terminal.

13. The method of claim 11 further including the step of acquiring said unprocessed medical imaging data at said medical imaging system.

14. The method of claim 11 further including the step of transmitting audio data from said medical imaging system to said remote terminal.

15. The method of claim 11 further including the step of transmitting system parameter data from said medical imaging system to said remote terminal.

16. A method for remotely post-processing medical imaging data, said method including the steps of:
    receiving unprocessed medical imaging data at a remote terminal; and
    post-processing said unprocessed medical imaging data,
    processing said unprocessed medical imaging data at said remote terminal according to preferences and control of an operator at said remote terminal;

scan converting said processed medical imaging data into pixel image data to form a medical image according to preferences and control of said operator at said remote terminal;

wherein said remote terminal processes said unprocessed medical information data according to imaging parameters and wherein said imaging parameters are controlled by an operator at said remote terminal and reflect operator preferences for image processing.

17. The method of claim 16 wherein said unprocessed medical imaging data is sent by a medical imaging system to said remote terminal.

* * * * *